(12) United States Patent
Jandrew et al.

(10) Patent No.: US 10,631,515 B2
(45) Date of Patent: Apr. 28, 2020

(54) PENTAS FLOWERS WITH A STAR PIGMENT PATTERN

(71) Applicant: Ball Horticultural Company, West Chicago, IL (US)

(72) Inventors: Jason Jandrew, Nipomo, CA (US); Alan D. Blowers, Elburn, IL (US); Monica J. Norby, Velva, ND (US)

(73) Assignee: Ball Horticultural Company, West Chicago, IL (US)

( * ) Notice: Subject to any disclaimer, the term of this patent is extended or adjusted under 35 U.S.C. 154(b) by 157 days.

(21) Appl. No.: 15/796,189

(22) Filed: Oct. 27, 2017

(65) Prior Publication Data

US 2018/0139919 A1    May 24, 2018

Related U.S. Application Data

(60) Provisional application No. 62/414,477, filed on Oct. 28, 2016.

(51) Int. Cl.
  *A01H 6/76* (2018.01)
  *A01H 5/02* (2018.01)
(52) U.S. Cl.
  CPC ............... *A01H 6/76* (2018.05); *A01H 5/02* (2013.01); *C12Y 101/01219* (2013.01)
(58) Field of Classification Search
  CPC .................................................. A01H 6/76
  See application file for complete search history.

(56) References Cited

U.S. PATENT DOCUMENTS

| | | | |
|---|---|---|---|
| 6,465,630 B1 | 10/2002 | Choi et al. | |
| 6,555,734 B2 | 4/2003 | Choi et al. | |
| 6,660,908 B2 | 12/2003 | Choi et al. | |
| PP19,055 P2 * | 7/2008 | Shiotsuki | A01H 5/02 |

FOREIGN PATENT DOCUMENTS

EP    1182257 B1    1/2005

OTHER PUBLICATIONS

Gou et al, The Plant Cell 23:1512-1522 (Year: 2011).*

* cited by examiner

*Primary Examiner* — David H Kruse
(74) *Attorney, Agent, or Firm* — Dentons US LLP

(57) ABSTRACT

The disclosure provides *Pentas* flowers comprising petals exhibiting an anthocyanin pigment star pattern, wherein said anthocyanin pigment star pattern is defined as comprising a substantial lack of anthocyanin pigment in the petal center and a presence of anthocyanin pigment in the petal margins. The disclosure also provides *Pentas* plants comprising a decreased level of dihydroflavonol reductase (DFR) transcripts resulting in an anthocyanin pigment star pattern and methods for producing a plant produced by crossing such plants with themselves or with another plant, such as a plant of another genotype. The disclosure further relates to seeds, plant parts, and plants produced by crossing *Pentas* plants of the disclosure with themselves or plants of a different genotype.

22 Claims, 1 Drawing Sheet

Specification includes a Sequence Listing.

SEQUENCE LISTING

```
<160> NUMBER OF SEQ ID NOS: 6

<210> SEQ ID NO 1
<211> LENGTH: 22
<212> TYPE: DNA
<213> ORGANISM: Artificial Sequence
<220> FEATURE:
<223> OTHER INFORMATION: Primer

<400> SEQUENCE: 1
gcgcatgtgt gaaaaatcaa tg                                           22

<210> SEQ ID NO 2
<211> LENGTH: 19
<212> TYPE: DNA
<213> ORGANISM: Artificial Sequence
<220> FEATURE:
<223> OTHER INFORMATION: Primer

<400> SEQUENCE: 2
gcaaccctgc tggtacatc                                               19

<210> SEQ ID NO 3
<211> LENGTH: 19
<212> TYPE: DNA
<213> ORGANISM: Artificial Sequence
<220> FEATURE:
<223> OTHER INFORMATION: Primer

<400> SEQUENCE: 3
cgagtccaar gaccctgag                                               19

<210> SEQ ID NO 4
<211> LENGTH: 21
<212> TYPE: DNA
<213> ORGANISM: Artificial Sequence
<220> FEATURE:
<223> OTHER INFORMATION: Primer

<400> SEQUENCE: 4
cawagatcat ccaaatgcac a                                            21

<210> SEQ ID NO 5
<211> LENGTH: 25
<212> TYPE: DNA
<213> ORGANISM: Artificial Sequence
<220> FEATURE:
<223> OTHER INFORMATION: Primer

<400> SEQUENCE: 5
gaataccata tccctgagtt gaatg                                        25

<210> SEQ ID NO 6
```

```
<211> LENGTH: 21
<212> TYPE: DNA
<213> ORGANISM: Artificial Sequence
<220> FEATURE:
<223> OTHER INFORMATION: Primer

<400> SEQUENCE: 6
ggaggaattc cattctcttg g                                          21
```

PENTAS FLOWERS WITH A STAR PIGMENT PATTERN

CROSS REFERENCE TO RELATED APPLICATIONS

This application claims the benefit of U.S. Provisional Application No. 62/414,477, filed Oct. 28, 2016, herein incorporated by reference in its entirety.

INCORPORATION OF SEQUENCE LISTING

A sequence listing containing the file named "BALL036US_ST25.txt" which is 2 kilobytes (measured in MS-Windows®) and created on Oct. 27, 2017, comprises 6 nucleotide sequences and is incorporated herein by reference in its entirety.

FIELD OF THE INVENTION

The present disclosure relates to the field of plant breeding and, more specifically, to *Pentas* plants having florets comprising altered anthocyanin pigment deposition resulting in florets showing petals with lighter-colored centers while maintaining their normally pigmented petal edges. Related methods and compositions for the production thereof are further provided.

BACKGROUND OF THE INVENTION

The goal of plant breeding is to combine various desirable traits in a single variety/hybrid. Such desirable traits may include any trait deemed beneficial by a grower and/or consumer, including desirable flower color or pattern, resistance to insects or disease and tolerance to environmental stress.

*Pentas lanceolata* is a species within the family Rubiaceae. The genus *Pentas* is comprised of approximately 35 herbaceous and semi-woody species located primarily in the Arabian Peninsula, Africa and Madagascar. The name *Pentas* comes from the Greek word for star, referring to the star shaped, five pointed petals. The nectar rich, tube-shaped florets of *Pentas lanceolata* appear massed in umbels as solid colors in shades of white, pink, rose, red and violet.

*Pentas lanceolata* is typically used as a pot or bedding plant and can be propagated from seeds or cuttings. *Pentas lanceolata* is a longtime favorite of Southern gardeners and landscapers due to its superb performance in hot, humid climates where many other species fail to thrive. *Pentas* blooms continuously all summer long and attracts butterflies and hummingbirds with its nectar rich flowers. Because of these advantageous performance and ornamental qualities, new *Pentas* hybrids exhibiting novel flower colors and patterns are highly desirable.

SUMMARY OF THE INVENTION

In one aspect, the present disclosure comprises *Pentas* flowers exhibiting an anthocyanin pigment star pattern, wherein said anthocyanin pigment star pattern is defined as comprising a substantial lack of anthocyanin pigment in the petal center and a presence of anthocyanin pigment in the petal margins. In some embodiments, said substantial lack of anthocyanin pigment is attributable to a decreased level of dihydroflavonol reductase (DFR) transcripts when compared to a flower of the same hue that lacks said pigment star pattern. The decreased level of anthocyanin pigment may be detected at the early bud, late bud, or open flower stage. Embodiments of the disclosure further provide a plant comprising a flower of the disclosure, or a seed that produces such a plant.

In another aspect, the disclosure provides *Pentas* plants comprising an allele conferring to the flowers of the plant an anthocyanin pigment star pattern, wherein said anthocyanin pigment star pattern is defined as comprising a substantial lack of anthocyanin pigment in the petal center and a presence of anthocyanin pigment in the petal margins, and wherein a representative deposit of seed comprising said allele has been deposited under NCMA Accession No. 20191202. In certain embodiments, the plant is a hybrid or an inbred. The disclosure further provides a plant part comprising a cell of a plant provided by the disclosure, for example a cutting, leaf, a floret, an ovule, pollen, or a flower. In other embodiments, the disclosure provides a seed that produces such a plant. The disclosure also provides a tissue culture of regenerable cells of a plant of the disclosure, for example a tissue culture comprising cells or protoplasts from a plant part selected from the group consisting of embryos, meristems, cotyledons, pollen, leaves, anthers, roots, root tips, pistil, flower, florets, seed, stems, and protoplasts or callus derived therefrom, or a plant regenerated from the tissue culture, wherein the regenerated plant exhibits said anthocyanin pigment star pattern.

In a further aspect, the disclosure provides a method of introducing a desired trait into a plant comprising: (a) crossing a plant according to claim 1 with a second plant that comprises a desired trait to produce F1 progeny; (b) selecting an F1 progeny that comprises the desired trait; (c) crossing the selected F1 progeny with a plant of the same variety as said plant according to claim 1 to produce backcross progeny; and (d) repeating steps (c) and (d) one or more times in succession to produce selected second or higher backcross progeny that comprise the desired trait. The disclosure further provides plants produced by the methods of the disclosure, wherein said plants exhibit said anthocyanin pigment star pattern.

In yet another aspect, the disclosure provides a method for producing *Pentas* seed comprising the steps of: (a) crossing a plant of the disclosure with itself or a second plant; and (b) collecting resulting seed. The method may further comprise a step of: (c) crossing a plant grown from said seed of step (b) with itself or a different plant at least one additional time to yield additional seed. In certain embodiments, the plant is a plant of *Pentas lanceolata* variety 'PAS1096472', a sample of seed of said *Pentas lanceolata* variety having been deposited under NCMA Accession No. 20191202.

In another aspect, the disclosure provides methods of producing a *Pentas* plant with an allele that confers an anthocyanin pigment star pattern comprising introgressing the allele from a plant of the disclosure into a plant of a different genotype. In some embodiments, the allele has been inherited from *Pentas lanceolata* variety 'PAS1096472' or a progeny of any generation thereof comprising said allele, a sample of seed comprising the allele having been deposited under NCMA Accession No. 20191202. The disclosure further provides F1 hybrid seed having a plant of the disclosure as one parent, for example wherein the parent is a male parent or a female parent.

BRIEF DESCRIPTION OF THE DRAWINGS

FIG. 1—Shows a representative *Pentas lanceolata* plant of variety 'PAS1096472' having petals with altered anthocyanin pigment deposition resulting in a star pigment pattern as described herein.

DETAILED DESCRIPTION OF THE INVENTION

The disclosure provides *Pentas* flowers comprising petals exhibiting an anthocyanin pigment star pattern, wherein said anthocyanin pigment star pattern is defined as comprising a substantial lack of anthocyanin pigment in the petal center and a presence of anthocyanin pigment in the petal margins. The anthocyanin pigment star pattern can be considered a picotee pattern to those skilled in the art. The substantial lack of anthocyanin pigment in the star pattern can be observed as a white petal color. The disclosure also provides *Pentas* plants and parts thereof comprising decreased level of dihydroflavonol reductase (DFR) transcripts in the flower. The presence of these reduced DFR transcripts and the resulting anthocyanin pigment star pattern is novel and not found in other varieties of *Pentas*, thus resulting in *Pentas* plants with flowers having petals with unique and previously unobserved star patterns. RNA transcript analysis of flower bud tissue from plants comprising the anthocyanin pigment star pattern of the disclosure and comparison against representatives of all known *Pentas* types revealed the biochemical distinctiveness of these petals, in addition to their unique appearance.

Anthocyanins are water soluble vacuolar pigments found throughout the tissues of vascular plants that confer orange, red, purple, and blue colors to the plant parts in which they accumulate. These compounds play key roles in the recruitment of pollinators and seed dispersers, signaling between plants and microbes, defense as antimicrobial agents, and UV protection (Winkel-Shirley, *Plant Physiol.* 126:485-493, 2001). Anthocyanins are derived from anthocyanidins, the aglycone form, by adding sugars to form glycosides and acyl glycosides. FIG. 1 shows a *Pentas lanceolata* plant having petals having altered anthocyanin pigment deposition resulting a star pigment pattern as described herein. Methods of assaying for anthocyanin content are known in the art.

A. Breeding *Pentas* Plants Comprising an Anthocyanin Pigment Star Pattern

The development of new varieties using one or more starting varieties is well known in the art and encompassed by the disclosure. In accordance with the disclosure, novel varieties may be created by crossing a plant of the disclosure followed by multiple generations of breeding according to such well-known methods. New varieties may be created by crossing with any second plant.

In selecting a second plant to cross with a plant of the disclosure, it will typically be preferred to choose those plants which either themselves exhibit one or more selected desirable characteristics or which exhibit the desired characteristic(s) when in hybrid combination. Once initial crosses have been made, selection takes place to produce new varieties. Examples of desirable traits may include, in specific embodiments, flower color or size, color patterning, foliage quality, floret size, shape and uniformity, maturity date, flower yield, seed germination rate, seedling vigor, disease tolerance or resistance, and adaptability for soil and climate conditions. Consumer-driven traits are other traits that may be incorporated into new plants developed by this disclosure.

One aspect of the current disclosure therefore provides methods for producing a plant comprising petals exhibiting an anthocyanin pigment star pattern. In certain embodiments, such a method may comprise: (a) crossing a *Pentas* plant comprising petals exhibiting an anthocyanin pigment star pattern with a second plant that comprises at least a first desired trait to produce F1 progeny; (b) selecting an F1 progeny that comprises the anthocyanin pigment star pattern and desired trait(s); (c) crossing the selected F1 progeny with itself or another *Pentas* plant; and (d) repeating steps (c) and (d) one or more times in succession to produce selected second or higher generation progeny that comprise petals exhibiting an anthocyanin pigment star pattern and one or more desired trait(s). In a particular embodiment, the second plant may be a *Pentas* plant and the progeny seed may be planted and grown to produce fertile hybrid progeny plants. A plant in accordance with the disclosure may be used in such crosses as the female plant or the male plant.

The disclosure also provides methods of producing *Pentas* plants comprising (a) crossing a *Pentas* plant comprising petals exhibiting an anthocyanin pigment star pattern as described herein with itself or a second plant capable of being crossed thereto; and (b) collecting resulting seed. In one embodiment, the second plant may be a *Pentas* plant. In some embodiments, the methods of the present disclosure may further comprise the step of (c) crossing a plant grown from said seed of step (b) with itself or a second plant at least one or more additional time(s) to yield additional seed. In another embodiment, the second plant may be a plant of *Pentas* variety 'PAS1096472.' Plants, seeds, and plant parts produced from the methods described herein and which comprise an anthocyanin pigment star pattern as described herein are also provided.

In certain embodiments, hybrid seeds may be produced using the methods of the present disclosure. A parent plant of such a seed may be a *Pentas* plant comprising petals exhibiting an anthocyanin pigment star pattern. In other embodiments, a plant as described herein may be either the male plant or the female plant in a given cross.

In accordance with the disclosure, any species of *Pentas* may be used. In particular, *Pentas* species that may be useful include but are not limited to *Pentas angustifolia, Pentas arvensis, Pentas caffensis, Pentas cleistostoma, Pentas glabrescens, Pentas herbacea, Pentas lanceolata* (Egyptian starcluster), *Pentas micrantha, Pentas nervosa, Pentas pauciflora, Pentas pubiflora, Pentas purpurea, Pentas purseglovei, Pentas suswaensis, Pentas tibestica, Pentas zanzibarica,* and the like.

In certain other embodiments, a plant of the disclosure may be an inbred plant, or may be a hybrid plant. In addition, a plant of the present disclosure may be homozygous for an allele that confers to the plant an anthocyanin pigment star pattern or a plant of the disclosure may be heterozygous for the allele.

In certain embodiments, the present disclosure provides plants modified using the methods described herein to include at least a first desired heritable trait. Such plants may, in one embodiment, be developed by backcrossing, wherein essentially all of the desired morphological and physiological characteristics of a variety are recovered in addition to a genetic locus transferred into the plant via the backcrossing technique. The term single locus converted plant as used herein refers to those plants which are developed by backcrossing, wherein essentially all of the desired morphological and physiological characteristics of a variety are recovered in addition to the single locus transferred into the variety via the backcrossing technique. By essentially all of the desired morphological and physiological characteristics, it is meant that the characteristics of a plant are recovered that are otherwise present when compared in the same environment, other than an occasional variant trait that might arise during backcrossing or direct introduction of a transgene.

Backcrossing can be used to improve a variety, and may be used, for example, to introduce an allele conferring an anthocyanin pigment star pattern into the plant genetic background of any plant that is sexually compatible with *Pentas*, as well as to introduce one or more traits into a plant of the disclosure. Backcrossing transfers a specific desired trait from one inbred or non-inbred source to a variety that lacks that trait. This can be accomplished, for example, by first crossing a variety of a desired genetic background (recurrent parent) to a donor inbred (non-recurrent parent), which carries the appropriate allele or loci for the desired trait(s) in question. The progeny of this cross are then mated back to the recurrent parent, followed by selection in the resultant progeny for the desired trait to be transferred from the non-recurrent parent. The process is repeated, for example for five or more backcross generations with selection for the desired trait, until a plant is obtained wherein essentially all of the desired morphological and physiological characteristics of the recurrent parent are recovered in the converted plant, in addition to the single transferred locus from the nonrecurrent parent. The progeny thus have the characteristic being transferred, but are like the superior parent for most or almost all other loci. The last backcross generation can be selfed to give true-breeding progeny when the trait being transferred is introgressed into a true-breeding variety.

The recurrent parent therefore provides the desired genetic background, while the choice of the particular non-recurrent parent will depend on the purpose of the backcross. One of the major purposes is to add some commercially desirable trait to the plant. The exact backcrossing protocol will depend on the characteristic or trait being altered and the genetic distance between the recurrent and nonrecurrent parents. Although backcrossing methods are simplified when the characteristic being transferred is a dominant allele, a recessive allele or an additive allele (between recessive and dominant) may also be transferred. In this instance it may be necessary to introduce a test of the progeny to determine if the desired characteristic has been successfully transferred.

Modified backcrossing may also be used with plants comprising petals exhibiting an anthocyanin pigment star pattern. This technique uses different recurrent parents during the backcrossing. Modified backcrossing may be used to replace the original recurrent parent with a variety having certain more desirable characteristics or multiple parents may be used to obtain different desirable characteristics from each.

B. Further Embodiments of the Invention

In other embodiments, the disclosure provides methods of vegetatively propagating a *Pentas* plant of the disclosure. Such a method may comprise the steps of: (a) collecting tissue capable of being propagated from said plant; (b) cultivating said tissue to obtain proliferated shoots; and (c) rooting said proliferated shoots to obtain rooted plantlets. In other embodiments, such a method may further comprise growing *Pentas* plants from the rooted plantlets. In still further embodiments, a plant of the disclosure is propagated by seed, wherein a plant comprising an allele conferring an anthocyanin pigment star pattern may be used as either a female or a male parent for producing progeny seed and plants.

Also provided are methods of producing a *Pentas* plant with an allele that confers an anthocyanin pigment star pattern, said method comprising introgressing the allele from a plant comprising such an allele into a plant of a different genotype. In certain embodiments, the allele may be inherited from *Pentas* variety 'PAS1096472' or a progeny of any generation thereof comprising the allele.

Many single locus traits have been identified that are not regularly selected for in the development of a new inbred but that can be improved by backcrossing techniques. Single locus traits may or may not be transgenic; examples of these traits include, but are not limited to, resistance to bacterial, fungal, or viral disease, or herbicide or insect resistance. These comprise genes generally inherited through the nucleus.

Direct selection may be applied where the single locus acts as a dominant trait. For this selection process, the progeny of the initial cross are assayed for viral resistance and/or the presence of the corresponding gene prior to the backcrossing. Selection eliminates any plants that do not have the desired gene and resistance trait, and only those plants that have the trait are used in the subsequent backcross. This process is then repeated for all additional backcross generations.

Selection of *Pentas* plants for breeding is not necessarily dependent on the phenotype of a plant and instead can be based on genetic investigations. For example, one can utilize a suitable genetic marker which is closely genetically linked to a trait of interest. One of these markers can be used to identify the presence or absence of a trait in the offspring of a particular cross, and can be used in selection of progeny for continued breeding. This technique is commonly referred to as marker assisted selection. Any other type of genetic marker or other assay which is able to identify the relative presence or absence of a trait of interest in a plant can also be useful for breeding purposes. Procedures for marker assisted selection are well known in the art. Such methods will be of particular utility in the case of recessive traits and variable phenotypes, or where conventional assays may be more expensive, time consuming or otherwise disadvantageous. Types of genetic markers which could be used in accordance with the disclosure include, but are not necessarily limited to, Simple Sequence Length Polymorphisms (SSLPs), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858, specifically incorporated herein by reference in its entirety), and Single Nucleotide Polymorphisms (SNPs).

C. Plants Derived by Genetic Engineering

Many useful traits that can be introduced by backcrossing, as well as directly into a plant, are those which are introduced by genetic transformation techniques. Genetic transformation may therefore be used to insert a selected transgene into a plant of the disclosure or may, alternatively, be used for the preparation of transgenes which can be introduced by backcrossing. Methods for the transformation of plants that are well known to those of skill in the art and applicable to many crop species include, but are not limited to, electroporation, microprojectile bombardment, *Agrobacterium*-mediated transformation and direct DNA uptake by protoplasts.

To effect transformation by electroporation, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wound tissues in a controlled manner.

An efficient method for delivering transforming DNA segments to plant cells is microprojectile bombardment. In this method, particles are coated with nucleic acids and delivered into cells by a propelling force. Exemplary particles include those comprised of tungsten, platinum, and preferably, gold. For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

An illustrative embodiment of a method for delivering DNA into plant cells by acceleration is the Biolistics Particle Delivery System, which can be used to propel particles coated with DNA or cells through a screen, such as a stainless steel or Nytex screen, onto a surface covered with target cells. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing the damage inflicted on the recipient cells by projectiles that are too large. Microprojectile bombardment techniques are widely applicable, and may be used to transform virtually any plant species.

*Agrobacterium*-mediated transfer is another widely applicable system for introducing gene loci into plant cells. An advantage of the technique is that DNA can be introduced into whole plant tissues, thereby bypassing the need for regeneration of an intact plant from a protoplast. Modern *Agrobacterium* transformation vectors are capable of replication in *E. coli* as well as *Agrobacterium*, allowing for convenient manipulations. Moreover, recent technological advances in vectors for *Agrobacterium*-mediated gene transfer have improved the arrangement of genes and restriction sites in the vectors to facilitate the construction of vectors capable of expressing various polypeptide coding genes. The vectors described have convenient multi-linker regions flanked by a promoter and a polyadenylation site for direct expression of inserted polypeptide coding genes. Additionally, *Agrobacterium* containing both armed and disarmed Ti genes can be used for transformation.

In those plant strains where *Agrobacterium*-mediated transformation is efficient, it is the method of choice because of the facile and defined nature of the gene locus transfer. The use of *Agrobacterium*-mediated plant integrating vectors to introduce DNA into plant cells is well known in the art (U.S. Pat. No. 5,563,055, incorporated herein by reference in its entirety). Transformation of plant protoplasts also can be achieved using methods based on calcium phosphate precipitation, polyethylene glycol treatment, electroporation, and combinations of these treatments.

A number of promoters have utility for plant gene expression for any gene of interest including but not limited to selectable markers, scoreable markers, genes for pest tolerance, disease resistance, and any other gene of agronomic interest. Examples of constitutive promoters useful for driving gene expression in plants include, but are not limited to, the cauliflower mosaic virus (CaMV) P-35S promoter, which confers constitutive, high-level expression in most plant tissues, including monocots; a tandemly duplicated version of the CaMV 35S promoter, the enhanced 35S promoter (P-e35S) the nopaline synthase promoter, the octopine synthase promoter; and the figwort mosaic virus (P-FMV) promoter as described in U.S. Pat. No. 5,378,619 (incorporated herein by reference in its entirety), and an enhanced version of the FMV promoter (P-eFMV) where the promoter sequence of P-FMV is duplicated in tandem, the cauliflower mosaic virus 19S promoter, a sugarcane bacilliform virus promoter, a commelina yellow mottle virus promoter, and other plant DNA virus promoters known to express in plant cells.

A variety of plant gene promoters that are regulated in response to environmental, hormonal, chemical, and/or developmental signals can be used for expression of an operably linked gene in plant cells, including promoters regulated by (1) heat, (2) light (e.g., pea rbcS-3A promoter; maize rbcS promoter; or chlorophyll a/b-binding protein promoter), (3) hormones, such as abscisic acid, (4) wounding (e.g., wun1); or (5) chemicals such as methyl jasmonate, salicylic acid, or Safener. It may also be advantageous to employ organ-specific promoters.

Exemplary nucleic acids which may be introduced to the plants of this disclosure include, for example, DNA sequences or genes from another species, or even genes or sequences which originate with or are present in the same species, but are incorporated into recipient cells by genetic engineering methods rather than classical reproduction or breeding techniques. However, the term "exogenous" is also intended to refer to genes that are not normally present in the cell being transformed, or perhaps simply not present in the form, structure, etc., as found in the transforming DNA segment or gene, or genes which are normally present and that one desires to express in a manner that differs from the natural expression pattern, e.g., to over-express. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA which is already present in the plant cell, DNA from another plant, DNA from a different organism, or a DNA generated externally, such as a DNA sequence containing an antisense message of a gene, or a DNA sequence encoding a synthetic or modified version of a gene.

Many hundreds if not thousands of different genes are known and could potentially be introduced into a plant comprising petals exhibiting an anthocyanin pigment star pattern according to the disclosure. Non-limiting examples of particular genes and corresponding phenotypes one may choose to introduce into a of the disclosure include one or more genes for insect tolerance, such as a *Bacillus thuringiensis* (B.t.) gene, pest tolerance such as genes for fungal disease control, herbicide tolerance such as genes conferring glyphosate tolerance, and genes for quality improvements such as environmental or stress tolerances, or any desirable changes in plant physiology, growth, development, morphology or plant product(s). For example, structural genes would include any gene that confers insect tolerance including but not limited to a *Bacillus* insect control protein gene as described in WO 99/31248, U.S. Pat. Nos. 5,689,052, 5,500,365 and 5,880,275, each of which are herein incorporated by reference in their entirety. In another embodiment, the structural gene can confer tolerance to the herbicide glyphosate as conferred by genes including, but not limited to *Agrobacterium* strain CP4 glyphosate resistant EPSPS gene (aroA:CP4) as described in U.S. Pat. No. 5,633,435, herein incorporated by reference in its entirety, or glyphosate oxidoreductase gene (GOX) as described in U.S. Pat. No. 5,463,175, herein incorporated by reference in its entirety.

Alternatively, the DNA coding sequences can affect these phenotypes by encoding a non-translatable RNA molecule that causes the targeted inhibition of expression of an endogenous gene, for example via antisense- or co-suppression-mediated mechanisms. The RNA could also be a catalytic RNA molecule (i.e., a ribozyme) engineered to cleave a desired endogenous mRNA product. Thus, any gene which produces a protein or mRNA which expresses a phenotype or morphology change of interest is useful for the practice of the present disclosure.

D. Definitions

In the description and tables herein, a number of terms are used. In order to provide a clear and consistent understanding of the specification and claims, the following definitions are provided:

Allele: Any of one or more alternative forms of a gene locus, all of which alleles relate to one trait or characteristic. In a diploid cell or organism, the two alleles of a given gene occupy corresponding loci on a pair of homologous chromosomes.

Anthocyanin: Anthocyanins are a group of plant pigments that generally occur in the plant as glycosides and acylglycosides of anthocyanidins, the aglycones. Anthocyanidins vary in the different hydroxyl or methoxy substitutions in their basic flavylium (2-phenylbenzopyrilium) structure. In accordance with the disclosure, a *Pentas* plant as described herein comprises anthocyanin pigment in the petal center and a presence of anthocyanin pigment in the petal edges resulting in an anthocyanin pigment star pattern. In particular, plants of the disclosure may comprise any percent reduction in the petal center compared with the petal edges. For example, such a plant may comprise a percent reduction in the petal center compared with the petal edges including, but not limited to at least about 0.1%, at least about 1%, at least about 10%, at least about 25%, at least about 50%, at least about 75%, at least about 80%, at least about 85%, at least about 90%, at least about 95%, at least about 96%, at least about 97%, at least about 98%, at least about 99%, at least about 99.5%, or at least about 100%, or more.

Backcrossing: A process in which a breeder repeatedly crosses hybrid progeny, for example a first generation hybrid (F1), back to one of the parents of the hybrid progeny. Backcrossing can be used to introduce one or more single locus conversions from one genetic background into another.

Crossing: The mating of two parent plants.

Cross-pollination: Fertilization by the union of two gametes from different plants.

F1 Hybrid: The first generation progeny of the cross of two non-isogenic plants.

Genotype: The genetic constitution of a cell or organism.

Phenotype: The detectable characteristics of a cell or organism, which characteristics are the manifestation of gene expression.

Picotee pattern: A flower color pattern in which the flower petals are primarily of one color with a petal margin of another, typically contrasting, color.

Plant Part: As used herein, a plant part refers to a part of a plant of the present disclosure. A plant part may be defined as comprising a cell of such plant, such as a cutting, a leaf, a floret, an ovule, pollen, a cell, a seed, a flower, an embryo, a meristem, a cotyledon, an anther, a root, a root tip, a pistil, a stalk, a stem, and a protoplast or callus derived therefrom.

Quantitative Trait Loci (QTL): Quantitative trait loci (QTL) refer to genetic loci that control to some degree numerically representable traits that are usually continuously distributed.

Regeneration: The development of a plant from tissue culture. In accordance with the disclosure, a regenerated *Pentas* plant as described herein would comprise the allele that confers a lack of anthocyanin pigment in the petal center and a presence of anthocyanin pigment in the petal edges resulting in an anthocyanin pigment star pattern.

Self-pollination: The transfer of pollen from the anther to the stigma of the same plant.

Single Locus Converted (Conversion) Plant: Plants which are developed by a plant breeding technique called backcrossing, wherein essentially all of the desired morphological and physiological characteristics of a *Pentas* variety are recovered in addition to the characteristics of the single locus transferred into the variety via the backcrossing technique and/or by genetic transformation.

Star pattern: A flower color pattern in which the shape of the base color of an individual petal resembles the point of a five-pointed star bordered with another, typically darker, color.

Substantially Equivalent: A characteristic that, when compared, does not show a statistically significant difference (e.g., p=0.05) from the mean.

Tissue Culture: A composition comprising isolated cells of the same or a different type or a collection of such cells organized into parts of a plant. A tissue culture in accordance with the disclosure may originate from or comprise cells or protoplasts from a plant part selected from the group consisting of embryos, meristems, cotyledons, pollen, leaves, anthers, roots, root tips, pistil, flower, florets, seed, stems, and protoplasts or callus derived therefrom.

E. Deposit Information

A deposit of *Pentas lanceolata* variety 'PAS1096472', disclosed above and recited in the claims, has been made with the Provasoli-Guillard National Center for Marine Algae and Microbiota (NCMA), 60 Bigelow Drive, East Boothbay, Me., 04544 USA. The date of the deposit is Dec. 3, 2019. The accession number for said deposited seeds of *Pentas lanceolata* variety 'PAS1096472' is NCMA Accession No. 20191202. Upon issuance of a patent, all restrictions upon the deposit will be removed, and the deposit is intended to meet all of the requirements of 37 C.F.R. § 1.801-1.809. The deposit will be maintained in the depository for a period of 30 years, or 5 years after the last request, or for the effective life of the patent, whichever is longer, and will be replaced if necessary during that period.

EXAMPLES

Although the foregoing disclosure has been described in some detail by way of illustration and example for purposes of clarity and understanding, it will be obvious that certain

Example 1

Discovery of Star Pattern in *Pentas*

Plants from a primarily red-flowered proprietary breeding line designated 5912 were observed to have florets showing petals with lighter-colored centers while maintaining their normally pigmented petal edges. The trait is believed to have recessive inheritance with one or more modifiers.

These unique plants were selected and self-pollinated. Seed from these self-pollinations was sown, and more plants showing lighter petal centers were selected. This population segregated pink flowers and red flowers each with lighter petal centers. Plants with florets showing the most distinct white petal centers were selected and given the family name 8021.

Plants of the 8021 family were self-pollinated to create seed which was sown. Plants from the 8021 family were also crossed to other solid color backgrounds and seed from both the self-pollinations and the crosses was sown. In the next generation, more plants with even more distinct white petal centers were selected from family 8021. Plants from the crosses with 8021 did not have very distinct white petal centers and so they were self-pollinated to achieve seed for the F2 generation. The newest seed from the 8021 family was sown as well as the F2 generation of crosses with this family. From the F2 crosses, more red and pink bicolor flowers were selected as well as new bicolors in lavender, violet and rose. These new color variants were selected and assigned the family numbers 8261, 8262 and 8336.

Recurrent selection was used to continue to stabilize this flower pattern for each of these families. The recurrent selection process was continued until lines 8021, 8261, 8262, and 8336 bred true to type for petal margin color and clear, distinct white petal centers. Next, crosses were made between these true to type parent lines for potential commercial hybrids including a line designated 'PAS1096472'. These hybrids were evaluated in greenhouse and field trials. The best performing bicolor hybrids were then placed in production trials. Exemplary lines exhibiting white petal centers and colored petal margins are shown in Table 1.

TABLE 1

Exemplary *Pentas* lines exhibiting a novel star pigment pattern.

| Accession | Color | Breeding families |
|---|---|---|
| #177 | Lavender Star | 8336 × 8259 |
| #352 | Pink Star | 8259 × 8262 × 8021 |
| #354 | Rose Star | 8504 × 8262 × 8021 |
| #358 | Violet Star | 8336 × 8262 × 8021 |
| #389 | Red Star | 8262 × 8021 × 8261 |
| #390 | Red Star | 8259 × 8261 |

Example 2

Characterization of *Pentas* Plants Exhibiting Star Flower Pigment Pattern

This example describes *Pentas* plants exhibiting the star pigment pattern provided by the disclosure. The descriptions and measurements relate to plants produced from seed and grown under conditions comparable to those used in commercial practice in the Midwestern United States. The plants were grown for approximately 10 weeks after being transplanted in flats having 18 cells per insert. Each cell was approximately 3⅛×3⅛×3 inches deep and contained soil-less growth medium. No supplemental lighting was provided. Measurements and numerical values represent averages of typical plants.

Of the many commercially available *Pentas* cultivars, the most similar in comparison to 'PAS1096472' is Graffiti Violet. However, in side-by-side comparison, plants of the new cultivar differ from plants of Graffiti Violet in at least the following characteristics:

i) Plants of 'PAS1096472' have a petal color pattern different from plants of Graffiti Violet;

ii) Plants of 'PAS1096472' have a petal color different from plants of Graffiti Violet; and iii) Plants of 'PAS1096472' have larger diameter corollas than plants of Graffiti Violet.

A further comparison of 'PAS1096472' with Graffiti Violet is provided in Table 2.

TABLE 2

Comparison of selected characteristics of 'PAS1096472' *Pentas* plants with Graffiti Violet *Pentas* plants.

| 'PAS1096472' | Graffiti Violet |
|---|---|
| Plant Description: | Plant Description: |
| Growth habit and general appearance - Moderately vigorous, upright-mounded. Size - Height from soil level to top of plant plane: Approximately 20.0 cm. Width: Approximately 24.0 cm. Root description - Fibrous, fine, white in color. Rooting habit - Freely branching, moderately dense. Branching habit - Freely basal branching, pinching not required. Aspect: Approximately 45° from center. Quantity of lateral branches: Approximately 4. Lateral branches - Strength: Strong. Length: Approximately 10.0 cm. Diameter: Approximately 3.0 mm. Length of central internode: Approximately 3.0 cm. Texture: | Growth habit and general appearance - Moderately vigorous, upright-mounded. Size - Height from soil level to top of plant plane: Approximately 22.5 cm. Width: Approximately 24.0 cm. Root description - Fibrous, fine, white in color. Rooting habit - Freely branching, moderately dense. Branching habit - Freely basal branching, pinching not required. Aspect: Approximately 45° from center. Quantity of lateral branches: Approximately 4. Lateral branches - Strength: Strong. Length: Approximately 11.0 cm. Diameter: Approximately 3.0 mm. Length of central internode: Approximately 3.0 cm. Texture: |

TABLE 2-continued

Comparison of selected characteristics of 'PAS1096472' Pentas plants with Graffiti Violet Pentas plants.

| 'PAS1096472' | Graffiti Violet |
|---|---|
| Densely pubescent. Color of young stems: 146B. Color of mature stems: 146A. | Moderately pubescent. Color of young stems: 146B. Color of mature stems: 146A. |

| Foliage Description: | Foliage Description: |
|---|---|
| General description - Fragrance: None detected. Form: Simple. Arrangement: Opposite.<br>Leaves - Aspect: Acute angle to stem. Shape: Elliptic to ovate. Margin: Entire. Apex: Acute. Base: Attenuate. Venation pattern: Pinnate. Length of mature leaf: Approximately 10.0 cm. Width of mature leaf: Approximately 5.0 cm. Texture of upper surface: Moderately pubescent. Texture of lower surface: Densely pubescent on venation. Color of upper surface of young and mature foliage: 137A with venation of 146D. Color of lower surface of young and mature foliage: Closest to 147B with venation of 147D.<br>Petiole - Length: Approximately 2.5 cm. Diameter: Approximately 3.0 mm. Texture: Densely pubescent. Color: 146D. | General description - Fragrance: None detected. Form: Simple. Arrangement: Opposite.<br>Leaves - Aspect: Acute angle to stem. Shape: Elliptic to ovate. Margin: Entire. Apex: Acute. Base: Attenuate. Venation pattern: Pinnate. Length of mature leaf: Approximately 8.5 cm. Width of mature leaf: Approximately 5.3 cm. Texture of upper surface: Moderately pubescent. Texture of lower surface: Sparsely pubescent on venation. Color of upper surface of young and mature foliage: 137A with venation of 146D. Color of lower surface of young and mature foliage: Closest to 147B with venation of 147D.<br>Petiole - Length: Approximately 1.5 cm. Diameter: Approximately 3.0 mm. Texture: Densely pubescent. Color: 146D. |

| Flowering Description: | Flowering Description: |
|---|---|
| Flowering habit - 'PAS1096472' is freely flowering under outdoor growing conditions with substantially continuous blooming from late spring through summer.<br>Lastingness of individual inflorescence on the plant - Approximately 3 to 4 weeks.<br>Inflorescence Description:<br>General description - Type: Compound corymbs. Aspect: Facing upward to slightly outward. Fragrance: None detected. Quantity per plant: Approximately 3. Diameter: Approximately 10.0 cm. Height: Approximately 4.5 cm.<br>Peduncle - Strength: Strong. Aspect: Erect to 45° from center. Length: Approximately 2.0 to 5.0 cm. Diameter: Approximately 2.0 mm. Texture: Densely pubescent. Color: 146B. | Flowering habit - Graffiti Violet is freely flowering under outdoor growing conditions with substantially continuous blooming from late spring through summer.<br>Lastingness of individual inflorescence on the plant - Approximately 3 to 4 weeks.<br>Inflorescence Description:<br>General description - Type: Compound corymbs. Aspect: Facing upward to slightly outward. Fragrance: None detected. Quantity per plant: Approximately 3. Diameter: Approximately 9.0 cm. Height: Approximately 5.0 cm.<br>Peduncle - Strength: Strong. Aspect: Erect to 45° from center. Length: Approximately 1.5 to 6.0 cm. Diameter: Approximately 2.0 mm. Texture: Densely pubescent. Color: 146B. |

| Flower Description: | Flower Description: |
|---|---|
| General description - Type: Single, rotate, not persistent. Quantity per inflorescence: Approximately 70.<br>Bud just before opening - Shape: Elliptic. Length: Approximately 6.0 mm. Width: Approximately 3.0 mm. Texture: Densely pubescent. Color: 145C.<br>Corolla - Diameter: Approximately 1.7 cm. Depth: Approximately 2.5 cm.<br>Petals - Quantity: 5, in a single whorl. Shape: Ovate. Margin: Entire. Apex: Acute. Base: Fused to corolla tube. Length from throat: Approximately 6.0 mm. Width: Approximately 5.0 mm. Texture of upper surface: Glabrous. Texture of lower surface: Sparsely pubescent. Color of upper surface when first and fully open: Margins of NN78C with centers of NN155D often with random streaks of NN78C. Color of lower surface when first and fully open: NN155D with an overlay of 75A.<br>Corolla tube - Diameter at throat: Approximately 5.0 mm. Diameter at base: Approximately 1.0 mm. Length: Approximately 1.8 cm. Texture of outer surface: Moderately pubescent. Texture of inner surface: Sparsely pubescent, throat | General description - Type: Single, funnelform, not persistent. Quantity per inflorescence: Approximately 50.<br>Bud just before opening - Shape: Elliptic. Length: Approximately 7.0 mm. Width: Approximately 3.0 mm. Texture: Densely pubescent. Color: 145C.<br>Corolla - Diameter: Approximately 1.3 cm. Depth: Approximately 2.8 cm.<br>Petals - Quantity: 5, in a single whorl. Shape: Ovate. Margin: Entire. Apex: Acute. Base: Fused to corolla tube. Length from throat: Approximately 7.0 mm. Width: Approximately 5.0 mm. Texture of upper surface: Glabrous. Texture of lower surface: Sparsely pubescent. Color of upper surface when first and fully open: N75C. Color of lower surface when first and fully open: NN155D with an overlay of N75C.<br>Corolla tube - Diameter at throat: Approximately 5.0 mm. Diameter at base: Approximately 1.0 mm. Length: Approximately 2.2 cm. Texture of outer surface: Sparsely pubescent. Texture of inner surface: Sparsely pubescent, throat opening densely pubescent. Color of outer surface: NN155D with longitudinal streaks of N75C. |

TABLE 2-continued

Comparison of selected characteristics of 'PAS1096472' Pentas plants with Graffiti Violet Pentas plants.

| 'PAS1096472' | Graffiti Violet |
|---|---|
| opening densely pubescent. Color of outer surface: NN155D with longitudinal streaks of NN78C. Color of inner surface: NN155D. Calyx - Shape: Star-shaped. Diameter: Approximately 8.0 mm. Depth: Approximately 3.0 mm. Sepals - Quantity: 5. Arrangement: in a single whorl. Shape: Lanceolate. Margin: Entire. Apex: Acute. Base: Fused. Length: Approximately 3.0 mm. Width: Approximately 1.0 mm. Texture of upper and lower surfaces: Sparsely pubescent. Color of upper surface when first and fully open: 137A. Color of lower surface when first and fully open: 137B. Pedicles - Strength: Strong. Aspect: Erect. Length: Approximately 2.0 mm. Diameter: Approximately 1.0 mm. Texture: Densely pubescent. Color: 145C. Reproductive organs - Androecium: Quantity per flower: 5, filaments adnate to corolla tube. Stamen length: Approximately 1.3 cm. Filament length of free portion: Approximately 1.0 mm. Filament color: NN155D with faint longitudinal streaks of N74D. Anther shape: Sagittate. Anther length: Approximately 2.0 mm. Anther color: NN155A. Pollen amount: Abundant. Pollen color: NN155B. Gynoecium: Quantity per flower: 1 per flower. Pistil length: Approximately 2.5 cm. Stigma shape: Bi-parted. Stigma length: 3.0 mm. Stigma color: 86A, pubescent. Style length: Approximately 2.1 cm. Style color: 145D. Ovary length: Approximately 2.0 mm. Ovary color: 145C. | Color of inner surface: NN155D. Calyx - Shape: Star-shaped. Diameter: Approximately 1.1 cm. Depth: Approximately 5.0 mm. Sepals - Quantity: 5. Arrangement: in a single whorl of two larger sepals and three smaller. Shape: Lanceolate. Margin: Entire. Apex: Acute. Base: Fused. Length: Approximately 6.0 mm and larger two of 9.0 mm. Width: Approximately 1.0 mm and larger two of 2.0 mm. Texture of upper and lower surfaces: Sparsely pubescent. Color of upper surface when first and fully open: 137A. Color of lower surface when first and fully open: 137B. Pedicles - Strength: Strong. Aspect: Erect. Length: Approximately 2.0 mm. Diameter: Approximately 1.0 mm. Texture: Densely pubescent. Color: 145C. Reproductive organs - Androecium: Quantity per flower: 5, filaments adnate to corolla tube. Stamen length: Approximately 1.5 cm. Filament length of free portion: Approximately 1.0 mm. Filament color: NN155D. Anther shape: Sagittate. Anther length: Approximately 2.0 mm. Anther color: NN155A. Pollen amount: Moderate. Pollen color: NN155B. Gynoecium: Quantity per flower: 1 per flower. Pistil length: Approximately 2.8 cm. Stigma shape: Bi-parted. Stigma length: 3.0 mm. Stigma color: NN155D, pubescent. Style length: Approximately 2.3 cm. Style color: 155C. Ovary length: Approximately 2.0 mm. Ovary color: 145C. |

The chart used in the identification of colors described herein is The R.H.S. Colour Chart of The Royal Horticultural Society, London, England, 2015 edition, except where general color terms of ordinary significance are used. The color values were determined in under natural light conditions at locations in the Midwest United States. The phenotype described represents an exemplary cultivar under specific environmental conditions. Accordingly, it is possible that the phenotype may vary somewhat with variations in the environment, such as temperature, light intensity, and day length, without, however, any variance in genotype.

Example 3

CHS and DFR Gene Expression Patterns in Solid Color- and Star Pattern-Containing Pentas Petals The novel star pattern exhibited by the Pentas flower petals suggested that either a defect in anthocyanin production and/or an accelerated rate of anthocyanin degradation within the acyanic regions was responsible for this phenotype. Since the former hypothesis, a defect in anthocyanin production, was more readily testable, this possibility was investigated first. Defects in anthocyanin production that lead to reduced anthocyanin deposition, no anthocyanins, or various anthocyanin-related deposition patterns (e.g., star and picotee patterns) can be generally attributed to either transcriptional or post-transcriptional regulatory mechanisms. In the case of transcriptional mechanisms, genetic mutations in either anthocyanin biosynthetic genes or genes encoding transcription factors which interact with those pathway genes can negatively impact anthocyanin production. Regarding anthocyanin structural genes, two of them, chalcone synthase (CHS) and dihydroflavonol reductase (DFR), have been implicated in other plant systems where defects in anthocyanin production have been described. This is due, in large part, to the fact that the metabolic intermediates in this portion of the anthocyanin pathway are colorless, and defects in either of these genes can lead to the accumulation of colorless flavonoid compounds. The Pentas CHS and DFR genes were investigated for their potential role in contributing to the novel star pattern described herein.

Pentas lanceolata is a member of the Rubiaceae family with no publicly available DNA sequence information for the two genes of interest. In the case of CHS, the nucleotide sequence of the cDNA from Coffea arabica, another member of the Rubiaceae family, was known. This cDNA sequence was used in a BLAST search to identify highly conserved regions within closely-related CHS open reading frames such that primers PEN CHS 5' and PEN CHS 3' (SEQ ID NO. 1 and SEQ ID NO:2) could be designed which could be tested for their ability to amplify that segment of the Pentas CHS cDNA. This primer pair allowed successful recovery of a partial cDNA clone from Pentas.

Regarding DFR, the nucleotide sequence of the cDNA from Coffea arabica was not publicly available. As a substitute, the sequence of the Gentiana triflora DFR cDNA was known, with G. triflora belonging to the same Gentianales taxonomic order as Pentas species. This cDNA sequence was used in a BLAST search to identify highly conserved regions within closely-related DFR open reading frames such that degenerate primers PEN DFR 5' and PEN DFR 3' (SEQ ID NO. 3 and SEQ ID NO:4) could be designed which could be tested for their ability to amplify that segment of the *Pentas* DFR cDNA. A partial cDNA clone was indeed recovered and sequenced, with the resulting sequence information permitting the design of two new primers which were specific for the *Pentas* DFR sequence (PEN DFR EXON 5' (SEQ ID NO. 5) and PEN DFR QENGIP 3' (SEQ ID NO:6)).

Total RNA was then isolated from the petals of several solid-color *Pentas* accessions using the reagent, TRIzol (Life Technologies). To recover partial cDNAs for CHS and DFR, the respective primer pairs were added to one-step reverse-transcriptase-PCR (RT-PCR) reactions using SuperScript III One-Step RT-PCR System with Platinum Taq DNA Polymerase (Life Technologies) kit reagents. In the initial reaction step, the reactions were incubated at 50° C. for 30 minutes to convert the RNA to single-stranded cDNA by the action of reverse transcriptase using either the CHS- or DFR-specific primers. The Taq DNA polymerase-mediated DNA amplification steps which immediately followed were conducted for 40 cycles as follows: i) 30 seconds denaturation at 94° C.; ii) 60 seconds primers annealing at either 60° C. (CHS) or 55° C. (DFR); iii) followed by primer extension at 72° C. for either 60 seconds (CHS) or 30 seconds (DFR). A final extension time of five minutes at 72° C. concluded the reactions. The amplicons were then electrophoresed on a 1.8% high-resolution agarose gel and visualized with EZ-Vision dye on a UV transilluminator. Inspection of the amplicons revealed successful amplification the expected CHS (~325-bp) and DFR (~435-bp) cDNA fragments. The CHS and DFR amplicons were subjected to DNA sequence analysis to verify that the correct genes had been recovered; subsequent BLAST analysis confirmed that the expected CHS and DFR partial cDNA fragments had been recovered from *Pentas*.

To continue the analysis, a collection of 16 *Pentas* lines displaying either solid-colored petals or star-patterned petals were grown in a greenhouse environment. The varieties with solid petal colors (10) included lavender (2), pink (2), red (1), rose (2), violet (1), and white (2). The star-patterned, bicolor varieties (6) included lavender 'PAS1096472', pink, rose, red (2), and violet. For each accession, tissue samples representing three different developmental stages of flower development were harvested. When *Pentas* flowers open, they are already fully pigmented, indicating that anthocyanin deposition has already taken place. Therefore, activation and expression of anthocyanin pathway-related genes proceeds long before flower opening so that transcription and translation of pathway-associated genes, and assembly of the metabolic pathway for anthocyanin biosynthesis and accumulation can occur. Two tissue samples from the flower bud stage were selected, one being in the very early bud stage while the bud was still extremely compact and the second being a later bud stage in which the bud had expanded in size. Lastly, a freshly-opened flower petal was selected as the third tissue sample. Total RNA was isolated as described previously (using TRIzol) from the three tissue types for all 16 accessions, thus creating 48 total RNA samples.

Initially, these 48 RNA samples were subjected to RT-PCR as described to assess their CHS gene expression levels. As shown in Table 3, it was observed that the CHS gene was constitutively expressed and transcript levels remained relatively constant at each of the developmental stages analyzed here. Moreover, the CHS transcript levels were high and did not differ to any significant extent between accessions. Most significantly, there were no marked differences in the CHS transcript levels between the lines with solid petal colors compared to the ones with the star patterns (both showed strong expression). Taken together these results indicated that CHS gene expression was essentially invariant and that transcriptional regulation of this constitutively-expressed gene was not a likely contributor to the star pattern in *Pentas* petals.

TABLE 3

CHS and DFR gene expression levels during *Pentas* flower development.

| Accession | Flower Pattern | CHS | | | DFR-5'/3' | | | DFR-EXON/QENGIP | | |
|---|---|---|---|---|---|---|---|---|---|---|
| | | Early Bud | Late Bud | Open Flower | Early Bud | Late Bud | Open Flower | Early Bud | Late Bud | Open Flower |
| Graffiti White | Solid | 5 | 5 | 5 | 5 | 4 | 4 | 5 | 5 | 5 |
| Graffiti Pink | Solid | 5 | 5 | 5 | 4 | 1 | 0 | 4 | 2 | 0 |
| Graffiti Rose | Solid | 5 | 5 | 4 | 3 | 1 | 0 | 5 | 1 | 1 |
| Graffiti Lavender | Solid | 5 | 4 | 4 | 4 | 4 | 4 | 2 | 2 | 3 |
| Graffiti Violet | Solid | 5 | 5 | 5 | 5 | 0 | 0 | 5 | 1 | 1 |
| Butterfly White | Solid | 5 | 5 | 5 | 5 | 5 | 5 | 5 | 5 | 5 |
| Butterfly Deep Pink | Solid | 5 | 5 | 4 | 2 | 0 | 0 | 3 | 0 | 0 |
| Butterfly Deep Rose | Solid | 5 | 5 | 5 | 2 | 0 | 0 | 4 | 1 | 2 |
| Butterfly Red | Solid | 5 | 5 | 5 | 5 | 5 | 5 | 5 | 5 | 5 |
| Butterfly Light Lavender | Solid | 5 | 5 | 4 | 5 | 5 | 5 | 5 | 5 | 5 |
| Lavender Star #177 | Star | 5 | 5 | 4 | 0 | 0 | 0 | 0 | 1 | 1 |
| Pink Star #352 | Star | 3 | 5 | 5 | 0 | 0 | 0 | 0 | 0 | 1 |
| Rose Star #354 | Star | 4 | 4 | 4 | 0 | 0 | 0 | 1 | 0 | 1 |
| Violet Star #358 | Star | 5 | 5 | 3 | 1 | 0 | 0 | 2 | 1 | 0 |
| Red Star #389 | Star | 5 | 5 | 5 | 0 | 0 | 0 | 3 | 1 | 0 |
| Red Star #390 | Star | 5 | 5 | 5 | 2 | 1 | 1 | 4 | 2 | 2 |

0 = Undetectable transcript level;
1 = Very low transcript level;
2 = Low transcript level;
3 = Moderate transcript level;
4 = High transcript level;
5 = Very high Transcript level Next, these same 48 RNA samples were subjected to RT-PCR as described previously to assess their DFR gene expression levels. Unlike what was observed for CHS, it became immediately evident that DFR transcript levels were widely variable, with variation noted between the different developmental stages, between accessions, and most importantly, between the varieties with solid color and star patterns (see Table 3). The white-flowering varieties, Graffiti White and Butterfly White, accumulated high levels of DFR transcripts at all three developmental stages. The lavender-flowering varieties, Graffiti Lavender and Butterfly Light Lavender, displayed DFR gene expression patterns similar to the white varieties, with high transcript levels observed at all developmental stages. The pink-flowering varieties, Graffiti Pink and Butterfly Deep Pink, displayed their highest DFR expression levels at the very early bud stage, but undetectable levels by the time of flower opening. The rose-flowering varieties, Graffiti Rose and Butterfly Deep Rose, showed moderate DFR expression levels at the very early bud stage, but transcripts were barely detectable or undetectable in the latter two developmental stages. The red-colored variety, Butterfly Red, showed abundant DFR transcripts throughout development. Finally, the only violet-colored variety, Graffiti Violet, showed high DFR transcript levels at the very early bud stage only. Overall, these 10 lines showed a variety of DFR gene expression patterns, with some lines showing strong, constitutive DFR expression throughout development (white, lavender and red) and others showing strongest DFR expression at the early bud stage only (pink, rose, and violet). However, all of them shared the common feature that DFR gene expression levels were at their maximum at the very early bud stage.

In the six lines displaying the star pattern, it was again evident that DFR transcript levels were widely variable among these accessions. 'PAS1096472', the lavender star patterned sample coded #177, showed no detectable DFR transcripts in any of the three developmental stages. The sample coded #352, having a pink star pattern, showed undetectable levels of DFR expression at the two bud stages, as well as the open flower stage. Like samples #177 and #352, the rose star patterned sample coded #354 also showed undetectable levels of DFR transcripts at all three developmental stages. The violet star patterned sample coded #358 accumulated very low levels of DFR transcripts at the very early bud stage only, and not in either of the later developmental stages. Finally, the two red star patterned samples coded #389 and #390 differed slightly as #389 had no detectable DFR transcripts while #390 displayed low or very low transcript levels throughout flower development. Taken together these results indicated that DFR gene expression was significantly perturbed in the Pentas varieties exhibiting the star pattern, with four of the six lines producing undetectable quantities of DFR transcripts and the remaining two lines expressing very low to low amounts.

A common feature shared by all six star pattern-displaying lines was that the DFR transcript levels were significantly lower when compared to expression levels in solid-colored petals. These differences were most dramatic in the solid lavender and lavender star lines which showed strong, constitutive DFR expression and no expression, respectively. While DFR expression patterns were largely at or below the limit of detection, it should be recalled that CHS gene expression patterns were both constitutive and strong. Thus the CHS gene expression results strongly support the argument that each of the 48 RNA samples were composed of similar quantities of RT-PCR-quality RNA. Taken together, the contrasting results for the CHS and DFR gene expression studies indicated that the extremely low DFR gene expression levels were not due to technical factors (e.g., poor RNA quality). Therefore, these collective results demonstrate that the DFR gene expression patterns are biologically relevant, and that the petal star pattern is due, at least in part, to a mis-regulation of the DFR gene in those lines. In the very early bud stage of solid-color flowers, DFR expression levels are at or near their peak (compared to the two other stages analyzed here), thus ensuring that the DFR enzyme is present and available to participate in the anthocyanin biosynthesis. In sharp contrast, in the very early bud stages of lines with the star patterns, very low to undetectable levels of DFR transcripts were observed. This defect in DFR gene expression appears to lead to depleted levels of DFR enzyme, which ultimately leads to lower anthocyanin production and reduced anthocyanin accumulation, especially in the center of the petal.

To further investigate the role of mis-regulation of DFR gene expression in the development of the star pattern, another series of DFR gene expression studies was conducted. In the first DFR expression study, degenerate primers were employed to detect DFR cDNAs. After DNA sequence information was obtained for the Pentas DFR gene, this permitted the design of another primer pair with greater specificity for Pentas. Also, in this example, the 5' primer was comprised of sequences derived from two adjacent exons, thus ensuring that only cDNAs from properly-spliced mRNAs would be amplified (i.e., no amplification from contaminating genomic DNA nor unspliced mRNA molecules). Following this strategy, PEN DFR Exon-5' (SEQ ID NO: 5) and PEN DFR QENGIP-3' (SEQ ID NO: 6) were designed to yield a ~250-bp partial cDNA fragment. The Taq DNA polymerase-mediated DNA amplification steps were conducted for 40 cycles as follows: i) 30 seconds denaturation at 94° C.; ii) 60 seconds primer annealing at 60° C.; iii) followed by primer extension at 72° C. for 30 seconds. A final extension time of five minutes at 72° C. concluded the reactions. In preliminary RT-PCR experiments, it was discovered that this primer pair was slightly more effective at detecting DFR transcripts and was able to detect lower quantities of the mRNA than the initial DFR-specific primer pair. Even with this increased sensitivity, the DFR gene expression results obtained with this primer pair were essentially identical to the ones initially obtained with the original PEN DFR-5'/PEN DFR-3' primer pair, as shown in Table 3. That is, for the solid-colored varieties like white, lavender, and red, DFR expression remained generally strong and constitutive. For the solid pink, rose, and violet varieties, DFR transcripts were highly abundant at the earliest bud stage before declining during the latter two developmental stages.

Regarding the star patterned lines, the primary differences were that barely detectable levels of DFR transcripts could now be observed at various developmental stages in 'PAS1096472' coded #177 (having a lavender star), #352 (having a pink star) and #354 (having a rose star), whereas in earlier experiments, their DFR transcripts were below the limit of detection. Even though DFR transcripts were now barely detectable, the gene expression patterns were both unpredictable and variable for these lines. The violet star patterned sample coded #358 also demonstrated reduced DFR expression levels compared to the solid-violet line. The samples coded #389 and #390, having a red star pattern, yielded essentially similar results with overall reduced DFR transcript accumulation compared to the solid-red petals.

Taken together, these results demonstrate that DFR mis-regulation is a hallmark of the Pentas petal star patterns. It is worth noting that both white-flowering varieties, Graffiti White and Butterfly White, displayed strong, constitutive DFR expression patterns in the bud and petal tissues analyzed here. Therefore, despite the lack of anthocyanin deposition, their DFR expression patterns are completely different, both in terms of transcript abundance and developmental timing, compared to DFR in the star pattern flowers. These stark differences show that the molecular defect which leads to solid white petals in *Pentas* is different from the defect which leads to the acyanic regions of the petal in the star pattern-exhibiting lines.

Without wishing to be bound by any theory, it is contemplated that the reduction in DFR transcript levels in the star petals may be due to the altered activity of a transcription factor which serves to boost DFR gene expression levels early in flower development. When this transcription factor is fully functional, DFR expression levels are transcriptionally induced to high levels, thus promoting DFR enzyme production leading to anthocyanin biosynthesis/deposition. However, if the interaction between the transcription factor(s) and DFR gene are negatively impacted by a mutation that affects the abundance or activity of the transcription factor(s), then DFR gene expression will not be up-regulated properly, leading to deficits in DFR enzyme levels, and ultimately anthocyanin accumulation/deposition.

What is claimed is:

1. A *Pentas lanceolata* flower exhibiting an anthocyanin pigment star pattern, wherein said star pattern is attributable to a decreased level of dihydroflavonol reductase (DFR) transcripts at the early bud, late bud, or open flower stage when compared to a flower of the same hue that lacks said pigment star pattern.

2. A plant comprising the flower of claim 1.

3. A seed that produces the plant of claim 2.

4. A *Pentas lanceolata* plant comprising an allele conferring to the flowers of the plant an anthocyanin pigment star pattern, wherein said star pattern is attributable to a decreased level of dihydroflavonol reductase (DFR) transcripts at the early bud, late bud, or open flower stage when compared to a flower of the same hue that lacks said pigment star pattern, and wherein a representative deposit of seed comprising said allele has been deposited under NCMA Accession No. 20191202.

5. The plant of claim 4, wherein the plant is hybrid.

6. The plant of claim 4, wherein the plant is inbred.

7. A plant part comprising a cell of the plant of claim 4.

8. The plant part of claim 7, further defined as a cutting, leaf, a floret, an ovule, pollen, or a flower.

9. A seed that produces the plant of claim 4.

10. A tissue culture of regenerable cells of the plant of claim 4.

11. The tissue culture according to claim 10, comprising cells or protoplasts from a plant part selected from the group consisting of embryos, meristems, cotyledons, pollen, leaves, anthers, roots, root tips, pistil, flower, florets, seed, stems, and protoplasts or callus derived therefrom.

12. A plant regenerated from the tissue culture of claim 11, wherein the regenerated plant exhibits said anthocyanin pigment star pattern.

13. A method of introducing a desired trait into a plant comprising:
(a) crossing a first plant according to claim 1 with a second plant that comprises a desired trait to produce F1 progeny;
(b) selecting an F1 progeny that comprises the desired trait;
(c) crossing the selected F1 progeny with a plant of the same variety as said first plant in step (a) to produce backcross progeny; and
(d) repeating steps (c) and (d) one or more times in succession to produce selected second or higher backcross progeny that comprise the desired trait.

14. A plant produced by the method of claim 13, wherein the plant exhibits said anthocyanin pigment star pattern of said first plant.

15. A method for producing *Pentas lanceolata* seed comprising the steps of:
(a) crossing a first plant according to claim 1 with itself or a second plant; and
(b) collecting resulting seed.

16. The method of claim 15, further comprising the steps of:
(c) crossing a plant grown from said seed of step (b) with itself or a different plant at least one additional time to yield additional seed.

17. The method of claim 15, wherein the first plant is a plant of *Pentas lanceolata* variety 'PAS1096472', a sample of seed of said *Pentas lanceolata* variety having been deposited under NCMA Accession No. 20191202.

18. A method of producing a *Pentas lanceolata* plant with an allele that confers an anthocyanin pigment star pattern, said method comprising introgressing the allele from the plant according to claim 4 into a plant of a different genotype.

19. The method of claim 18, wherein said allele has been inherited from *Pentas lanceolata* variety 'PAS1096472' or a progeny of any generation thereof comprising said allele, a sample of seed comprising the allele having been deposited under NCMA Accession No. 20191202.

20. An F1 hybrid seed having the plant of claim 4 as one parent.

21. The F1 hybrid seed of claim 20, wherein said plant is a male parent.

22. The F1 hybrid seed of claim 20, wherein said plant is a female parent.

* * * * *